United States Patent [19]

Muccio

[11] Patent Number: 4,919,148
[45] Date of Patent: Apr. 24, 1990

[54] APPARATUS AND METHOD FOR TRANSCUTANEOUS ELECTRICAL STIMULATION

[76] Inventor: Philip E. Muccio, 753 Quilliams Rd., South Euclid, Ohio 44121

[21] Appl. No.: 218,710

[22] Filed: Jun. 13, 1988

[51] Int. Cl.⁵ .............................................. A61N 1/04
[52] U.S. Cl. .................................. 128/798; 128/799; 128/802; 128/803
[58] Field of Search .............................. 128/639–641, 128/644, 798, 799, 802, 803

[56] References Cited

U.S. PATENT DOCUMENTS

| | | | |
|---|---|---|---|
| 2,632,447 | 3/1953 | Dobes | 128/798 |
| 3,474,775 | 10/1969 | Johnson | 128/639 |
| 4,016,868 | 4/1977 | Allison | 128/644 |
| 4,092,985 | 6/1978 | Kaufman | 126/798 |
| 4,196,737 | 4/1980 | Bevilacqua | 128/798 |
| 4,300,575 | 11/1981 | Wilson | 128/798 |
| 4,381,012 | 4/1983 | Russek | 128/644 |
| 4,458,696 | 7/1984 | Larimore | 128/798 |
| 4,580,572 | 4/1986 | Granek et al. | 128/649 |
| 4,583,547 | 4/1986 | Granek et al. | 128/639 |

FOREIGN PATENT DOCUMENTS 0193480 9/1986 European Pat. Off. ............ 128/798

Primary Examiner—Lee S. Cohen
Attorney, Agent, or Firm—D. Peter Hochberg; Mark Kusner; Louis J. Weisz

[57] ABSTRACT

Electrode assembly for transcutaneous neural stimulation comprising a first layer of non-conductive knit fabric material; a flexible, generally flat electrically conductive electrode in confronting relationship with a portion of the fabric material; a second layer of non-conductive material overlying the upper surface of the electrode and dimensioned to extend beyond the periphery of the electrode; means for securing the second layer to the first layer to confine the electrode therebetween and define a generally flat pocket between the electrode and first layer, the pocket operable to receive a conductive fluid therein; and means defining a boundary around the periphery of the electrode for preventing migration of the conductive fluid beyond the periphery of the electrode.

17 Claims, 5 Drawing Sheets

APPARATUS AND METHOD FOR TRANSCUTANEOUS ELECTRICAL STIMULATION

FIELD OF INVENTION

The present invention pertains to a medical appliance and method for transcutaneous transmission of electrical signals, and more particularly to an electrode assembly to be positioned against a body of a living being for transcutaneous nerve stimulation or monitoring of body functions. The electrode assembly is particularly applicable for use as part of a body garment for electrically stimulating muscle tissue and will be described with particular reference thereto, although the present invention has other, broader application such as monitoring body functions or nerve stimulation to relieve pain.

BACKGROUND OF INVENTION

In transcutaneous electrical stimulation, the positioning and surface contact of the electrode in relation to the skin of the patient to be stimulated is very important. For optimum results, it is necessary that the electrode be accurately positioned in relation to the muscle and nerve to be stimulated and that good surface contact exists between the electrode and the skin to ensure maximum transmission of electrical stimulation to the nerve. It is widely known that skin tissue, in and of itself, is a relatively poor conductor of electrical stimulation because of its relative dryness. To overcome this problem, it has been known to "wet" the skin with a conductive fluid, such as water or a gel material, to increase electrical transmission therethrough. U.S. Pat. Nos. 4,583,547 and 4,580,572 to Granek et al disclose garments of a non-conductive web material having a plurality of electrodes connectable to a source of electrical stimulation positioned thereon. A space is defined between the web material and each electrode into which a conductive fluid is inserted. The conductive fluid seeps through the small interstices in the garment fabric to "wet" the skin. Stimulation is thus carried through the fabric by means of the conductive fluid.

A problem with such an electrode and garment is that the conductive fluid which wets the skin is not confined to a specific area below the electrode. In the embodiments shown, as the gel penetrates the garment to wet the skin it may also ooze or migrate beyond the outer periphery of the electrode. In this respect, gel migrating beyond the periphery or outer perimeters of the electrode may affect the net charge distribution from the electrical stimulation. In other words, as the conductive fluid migrates beyond the electrode, the area of conductance between the skin and the electrode increases substantially, and for a given current, the current density (i.e. amperage per square inch) decreases. For example, if a 25 milliamp current is delivered to a circular electrode having an area of 8 square inches (the radius of a circle having an area of 8 square inches is approximately 1.6 inches), the current density is approximately 3.125 milliamps per square inch. If the radius of this circle were to increase by 0.4 inches (the result of the oozing or migration of the conductive fluid), the area would increase to 12.6 square inches and the current density would decrease to 1.98 milliamps per square inch. Such as a drop is in the magnitude of approximately 33%. To maintain the same current density to the skin, the stimulator output must be increased by approximately one-third. As can be seen, the inability to maintain the gel within a clearly defined space beneath the electrode greatly reduces the reliability and accuracy of the electrode and the garment.

Another problem with garments of the type shown in the aforementioned patents to Granek et al., is that because the electrodes are relatively small there is little room for error with respect to positioning the electrode on the garment so that it aligns wih the "motor point" on the body of the wearer. The term "motor point" refers to the location on the surface of the skin where our electrical stimulus most easily elicits a muscle contraction. The location of these points on the body is conventionally known throughout the industry, however the spacing between respective points on the body will vary depending upon the size of the given individual. In this respect, garments with small electrodes are generally limited in use to a specific individual, or to individuals with very similar stature. Larger electrodes on garments would provide a greater likelihood of overlaying a "motor point" and therefore are preferable. However, with larger electrodes, should migration of the conductive fluid beyond the periphery of the electrodes occur, a substantial increase in the contact area results with a decrease in the current density.

These and other problems are overcome by the present invention wherein an electrode assembly is provided which confines the conductive fluid within a predetermined area beneath the electrode, and thereby enables more accurate and effective stimulation of the muscle tissue. By being able to accurately control the area wetted by the conductive gel, larger electrodes may be used to ensure operative contact with the wearer's motor points.

SUMMARY OF THE INVENTION

In accordance with the present invention there is provided an electrode assembly for transcutaneous neural stimulation. The electrode assembly includes a first layer of a non-conductive, knit fabric material. A flexible, generally flat electrically conductive electrode having an upper surface and a generally planar lower surface is provided, the lower surface being in confronting relationship with a portion of the fabric material. The electrode is connectable to a source of electrical stimulation. A second layer of a non-conductive material is provided to overlay the upper surface of the electrode. The second layer is dimensioned such that a portion thereof extends beyond the periphery of the electrode. Means are provided for securing the second layer on nonconductive material to the first layer of knit fabric material to confine the electrode therebetween. A generally flat pocket or cavity adapted to receive a conductive fluid is defined between the first layer of fabric material and the lower surface of the electrode. Means are provided defining a boundary around the periphery of the electrode for preventing migration of the conductive fluid beyond the periphery of the electrode.

In accordance wih another aspect of the present invention, there is provided a garment for transcutaneous neural stimulation comprising a garment made of electrically non-conducting knit material having an inner side to be positioned against the patient's body and an outer side. One or more generally flat, electrically conductive electrodes is provided on the outside of the knit material. Each electrode has an upper surface and a generally planar lower surface wherein the lower surface is in confronting relationship with a portion of the outer side of the fabric material. A layer of a non-conductive material is provided to overlay the upper surface of each electrode. This layer is dimensioned such as that a portion thereof extends beyond the periphery of each electrode. Means are provided for securing the layer to the garment to confine the electrode therebetween wherein a generally flat pocket or cavity adapted to receive a conductive fluid is defined between the garment and the lower surface of the electrode. Means are provided for defining a boundary around the periphery of the electrode which boundary prevents migration of the conductive fluid beyond the periphery of the electrode.

It is an object of the present invention to provide a device which permits automatic and easy location of electrodes on the body of patient.

Another object of the present invention is to provide a device such as described above which enables electrodes to be accurately located at specific body locations in a simple, repeatable and expedient manner.

Another object of the present invention is to provide an electrode assembly for use in a garment, which assembly confines conductive fluid within a known space for more accurate and efficient electrical stimulation.

Another object of the present invention is to provide an electrode assembly which is described above which is more comfortable to the wearer when used in a garment.

These and other objects and advantages of the invention will become apparent from the following description of embodiments thereof taken together with the accompanying drawings.

BRIEF DESCRIPTION OF THE DRAWINGS

The invention may take physical form in certain parts and arrangement of parts, preferred embodiments of which will be described in detail in this specification and illustrated in the accompanying drawings wherein.

DETAILED DESCRIPTION OF PREFERRED EMBODIMENT

Figure 1:
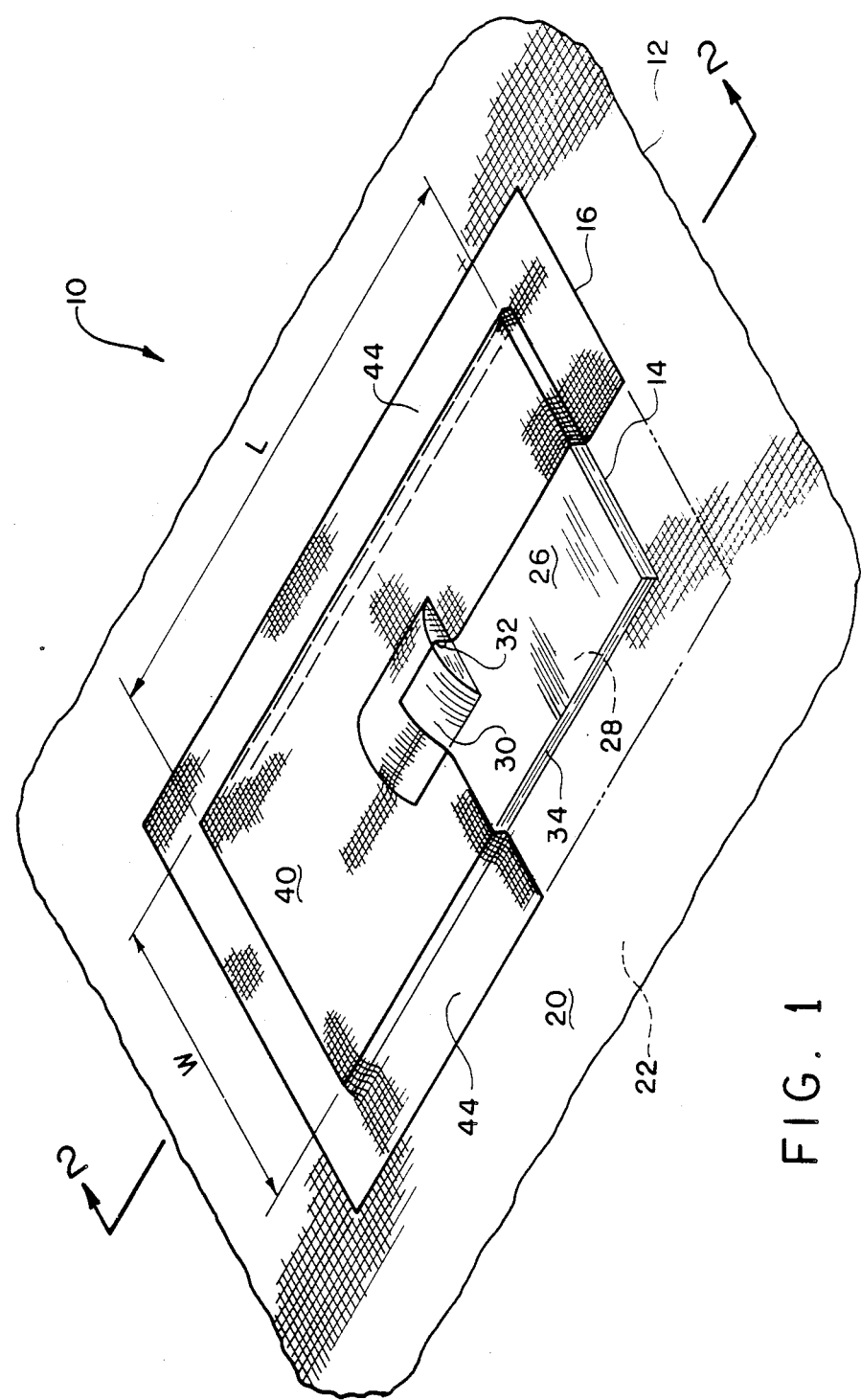
FIG. 1 is a perspective, partially sectioned, view showing the upper side of an electrode assembly illustrating a preferred embodiment of the present invention.

Referring now to the drawings wherein the showings are for the purpose of illustrating preferred embodiments of the present invention and not for the purpose of limiting the same, FIG. 1 shows an electrode assembly 10 for a transcutaneous neural stimulation. The electrode assembly 10, and the elements comprising the same, will hereinafter be described with reference to their respective positions relative to the patient on which the electrode assembly 10 is used. In this respect, the side or surface of the electrode or elements facing the patient will be referred to as the "lower" or "inner" side or surface, and the side or surface facing away from the patient shall be referred to as the "upper" or "outer" side or surface. Accordingly, FIG. 1 shows the outer surface of electrode assembly 10. Electrode assembly 10 is basically comprised of a first layer 12 of an electrically non-conductive material, an electrode 14 and an overlying second layer 16 of an electrically non-conductive material.

Layer 12 is generally comprised of a tight-knit, woven fabric material having an upper surface 20 and lower surface 22. The woven fabric material is preferably stretchable and includes interstices (not shown) defined by the yarns of the fabric material. Importantly, the fabric material is preferably tight-knit having small interstices to retard migration of fluid therethrough. In this respect, the small interstices will not prevent a fluid from seeping through the fabric material. They will however retard and reduce the amount of fluid which can penetrate through the material. In the context of the present invention, this reduced amount of fluid which can penetrate through the fabric is still sufficient to thoroughly wet the fabric material (i.e. penetrate through the material) and conduct electrical stimulation therethrough. On the other hand, the tight-knit fabric prevents excessive oozing or migration of the fluid therethrough, which migration produces the undesirable results previously mentioned. Thus, layer 12 is preferably comprised of a tight-knit, woven fabric material having interstices of a size operable to allow penetration therethrough of only sufficient fluid to wet the fabric material. According to the preferred embodiment, layer 12 is comprised of a stretch fabric material (Spandex TM) made from a blend of 90% nylon and 10% polyester. Such material provides the small interstices as described above, and in addition, due to its stretching characteristic, accommodates expansion and development in muscle tissue which may occur in patients over periods of time. In other words, a garment formed from a stretchable material conforms easily to variation in the body structure and can be utilized as a patient's body develops and changes.

Figure 2:
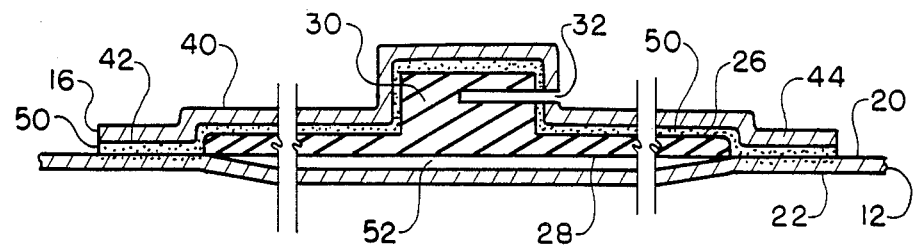
FIG. 2 is a sectional view taken along line 2—2 of FIG. 1.
Figure 3:
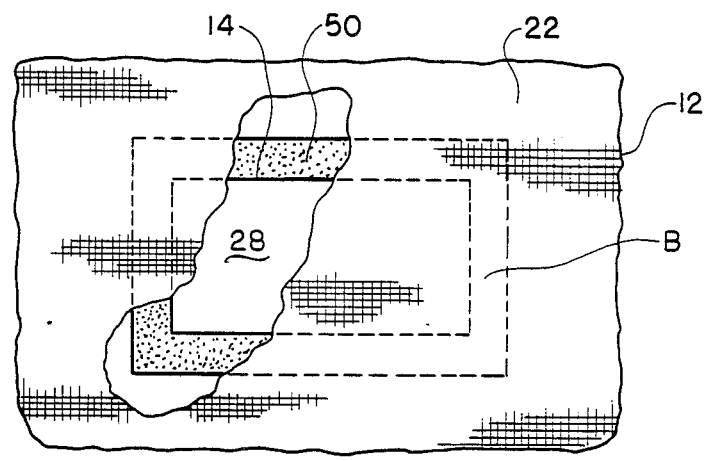
FIG. 3 is a reduced, partially sectioned view of the electrode assembly shown in FIG. 1 showing the lower side thereof.

Electrode 14 is generally flat and has a planar upper surface 26, and a planar lower surface 28. A centrally located, semi-cylindrical boss 30 extends from upper surface 26. A cylindrical bore 32 is provided in boss 30 (as best seen in FIG. 2) to receive a pin connector (not shown) attached to a source of electrical stimulation. In the embodiment shown, electrode 14 is generally rectangular in shape and defines a rectangular edge or periphery 34. In the drawings, the length of electrode 14 is designated "L" and the width of electrode 14 is designated "W". According to the present invention, electrode 14 preferably has a predetermined length "L" related to the portion of the body to be stimulated, as will be discussed in greater detail below. Electrode 14 is positioned above layer 12 with lower surface 28 of electrode 14 confronting upper surface 20 of layer 12. Electrode 14 is formed of an electrically conductive carbon material having a rubber-like consistency which provides flexibility thereto. In this respect, electrode 14, because of its relative thin profile is generally flexible and can bend to conform to the contours of the wearer as will be understood from a further reading of this description.

Layer 16 is comprised of an electrically non-conductive material and includes an outer or upper surface 40 and an inner or lower surface 42. Layer 16 overlies electrode 14 with lower surface 42 thereof confronting upper surface 26 of electrode 14. Layer 16 is dimensioned to extend beyond the edge or periphery 34 of electrode 14. The portion of layer 16 extending beyond edge 34 of electrode 14 is designated 44 in the drawings. According to the present invention, extending portion 44 of layer 16 is secured to layer 12 with electrode 14 confined therebetween. In the embodiment shown, layer 16 is secured to layer 12 by means of an adhesive layer 50 disposed subjacent lower surface 42, as best seen in FIG. 2. The thickness of adhesive layer 50 has been exaggerated in the drawings for the purposes of illustration. As seen in FIG. 2, layer 50 also secures layer 16 to upper surface 26 of electrode 14. A pocket or cavity 52 is defined between lower surface 28 of electrode 14 and upper surface 20 of layer 12. Cavity 52 has been exaggerated in the drawings for the purpose of illustration. In actuality, the stretch material of layer 12 is drawn into contact with lower surface 28 of electrode 14. Importantly, the adhesive material below extending portion 44 seeps into the interstices of the knit fabric comprising layer 12, and hardens therein as pictorially illustrated in FIG. 2. This hardening of the adhesive material in the interstices of the fabric material prevents fluid from seeping into the cloth through the interstices, and thus creates in effect a lateral barrier or boundary to fluids.

Cavity 52 is adapted to receive a measured amount of a conductive fluid or gel therein. A known conductive gel is available under the name of SIGNAGEL (trademark) Electrode Gel, and is distributed by Parker Laboratories of Orange, N.J. In the embodiment shown, a measured amount of such conductive gel may be inserted into cavity 52 by means of a piston-type syringe through layer 12. In this respect, as set forth above, layer 12 is preferably formed of an elastic, stretch-type material. By pinching the fabric immediately below the electrode, it may be stretched away from surface 28 of electrode 14 and the conductive gel injected into cavity 52 with a syringe. Gel may then be spread or disbursed throughout cavity 52. The interstices of the disclosed material permits gel to saturate or "wet" the fabric layer 12. Importantly, gel is maintained immediately below electrode 14. In this respect, the adhesive material which penetrated into layer 12 forms an effective boundary, designed B, which inhibits migration of gel. In other words, the adhesive material which secures extending portion 44 of overlying layer 16 to fabric layer 12 confines gel to the rectangular area or pocket 52 beneath electrode 14. Moreover, as seen in FIG. 2, adhesive layer 50 prevents gel from oozing around the upper edge 34 of electrode 14 to the upper surface 26 thereof, and thus prevents "wetting" of any outer surface of the electrode assembly. This reduces the likelihood of shock from contact with the outer surface of the electrode assembly. In effect, adhesive layer 50 seals the upper and outer surface of the electrode from the operative area beneath the electrode 14. By confining gel to a specific, defined area beneath the electrode 14, greater control over the area of stimulation is provided which in turn provides more accurate and reliable stimulation of specific locations on the body.

Figure 4:
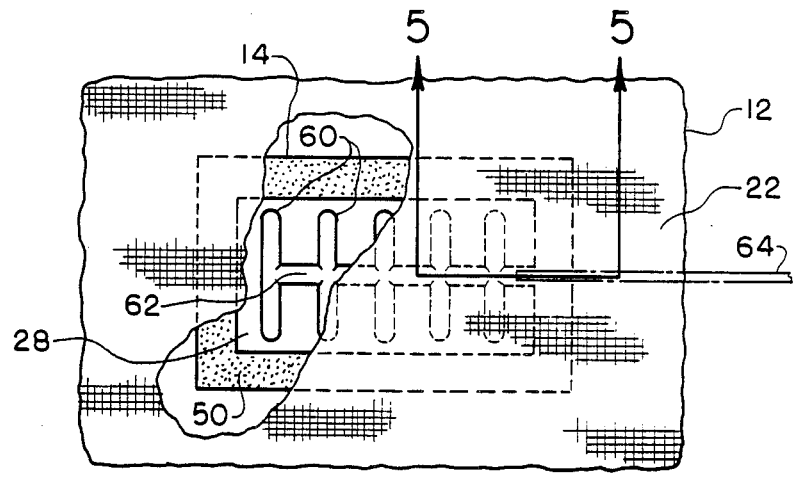
FIG. 4 is a partially sectioned view of an electrode assembly showing an alternate embodiment of the present invention.
Figure 5:
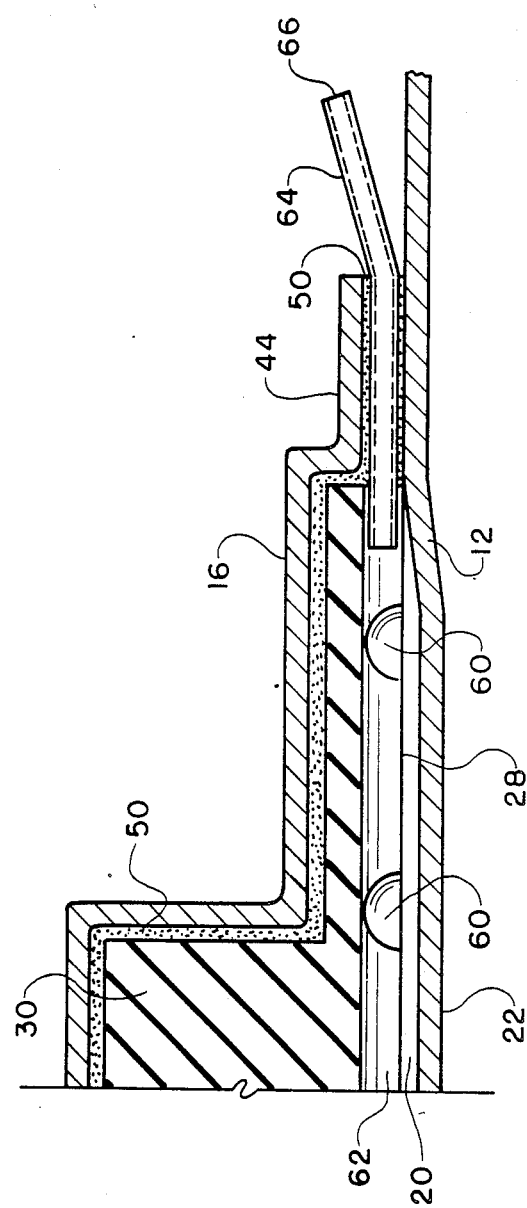
FIG. 5 is an enlarged sectional view taken along line 5—5 of FIG. 4.

FIGS. 4 and 5 show an alternate embodiment of electrode assembly 10. In this embodiment, a plurality of channels 60 are molded or otherwise formed in the lower surface 28 of electrode 14. Channels 60 are connected to each other by a branch channel 62, which extends to one end of electrode 14. A tubular member 64 is disposed between layer 12 and layer 16 with one end positioned within pocket 52 and branch channel 62, and the other end disposed above layer 12. Tubular member 64 includes an inner passageway 66 which is in communication with branch channel 62. As is apparent, with this embodiment gel 64 may be inserted into pocket 52 by means of passage 66 in tubular member 64. Whereas the embodiment shown in FIGS. 1 and 2, required that the conductive fluid be inserted in cavity or pocket 52 before the assembly 10 is placed in contact with he body, this embodiment provides means for inserting the conductive fluid while the electrode assembly is already on the body of the patent. This feature finds advantageous application when assembly 10 is used on a garment as will herinafter be described.

Figure 6:
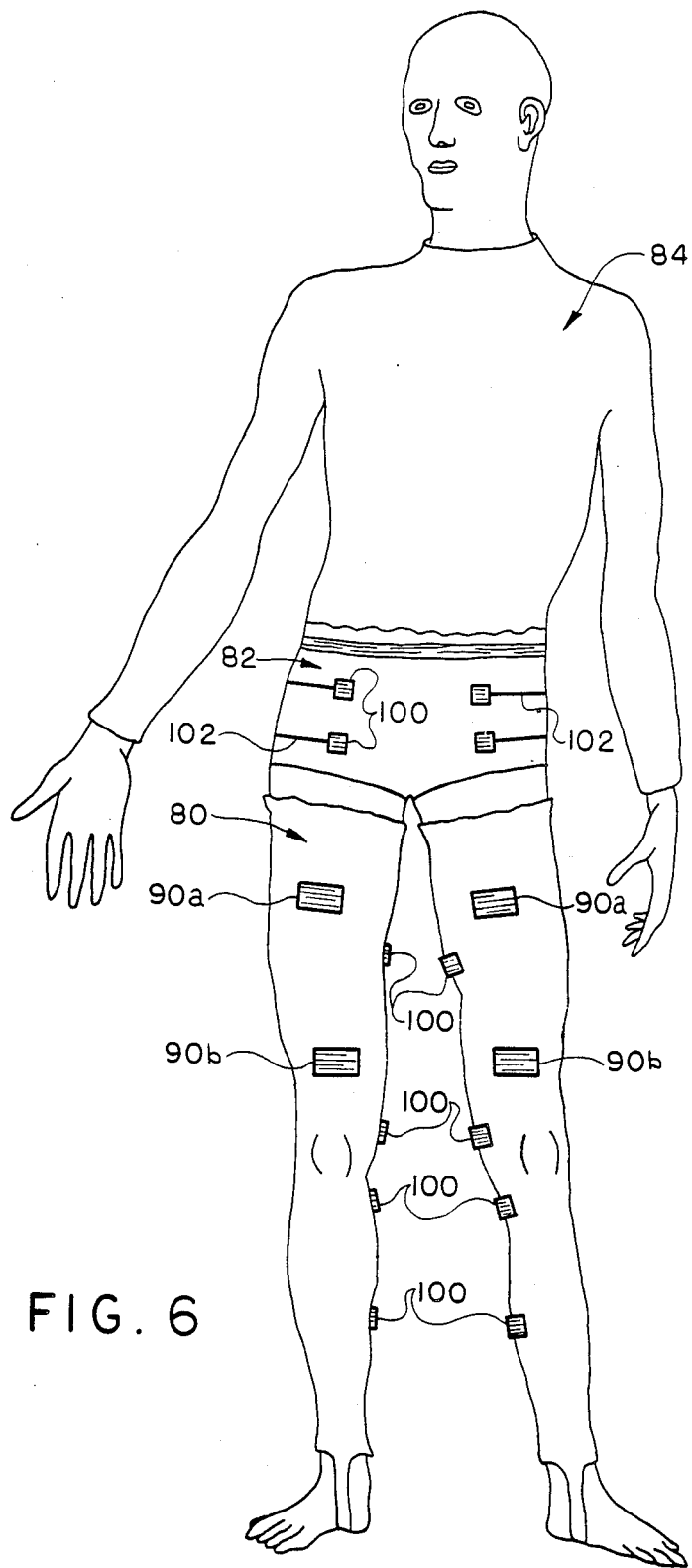
FIG. 6 is a front view of a garment illustrating another embodiment to the present invention.
Figure 7:
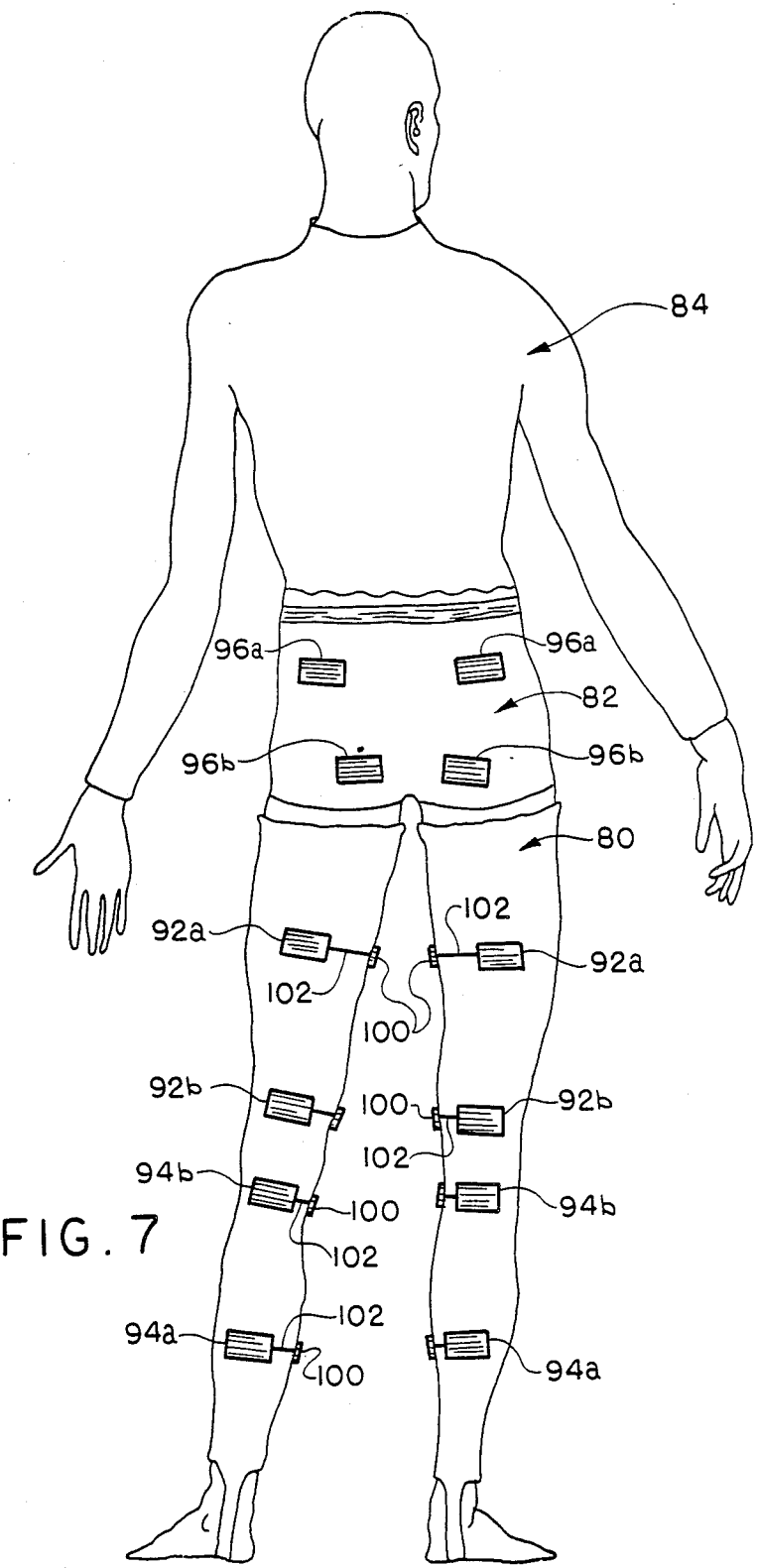
FIG. 7 is a back view of the garment shown in FIG. 6.

Electrode assembly 10 described heretofore is preferably used, and finds advantageous application, on body garments such as those shown in FIGS. 6 and 7. Garments may take the form of pants 80 (shown in section without a seat area), briefs 82, or a shirt 84, or combinations thereof, Garments 80, 82, and 84 are preferably formed of the stretch fabric material forming layer 12 as described above. A plurality of electrode assemblies 10 are provided at predetermined locations on the garments to correspond to "motor points" on the body of the patient to be stimulated. The electrode assemblies are grouped in pairs, each pair having an active electrode which is placed over the motor point and a ground electrode located at some adjacent location. In this respect, the active (positive) electrode and the ground (negative) electrode of a pair area located along a major muscle group. For example, one pair 90$a$, 90$b$ is positioned along the quadriceps, another pair 92$a$, 92$b$ along the hamstrings, another pair 94$a$, 94$b$ is positioned along the plantarflexers, and another pair 96$a$, 96$b$ is positioned along the gluteals. With respect to these electrodes, those bearing the suffix "a" are the active (positive) electrodes and those bearing the suffix "b" are the ground (negative) electrodes. To enable the wearer or more easily connect the electrodes on the back or posterior side of the garments to a source of electrical stimulation, intermediate connectors 100, attached to the operative electrodes by a flexible conductor 102, are provided at more accessible locations on the garments. In this respect, on pants 80, connectors are provided for the quadricep electrodes 90$a$, 90$b$ and the plantarflexers electrodes 94$a$, 94$b$ generally along a line extending along the inner leg as shown in the drawings. With respect to briefs 82, connectors 100 are provided on the anterior or front side of the garment and are connected by conductors 102 to the gluteals electrodes 96$a$, 96$b$ on the posterior of the garment. With such an arrangement, all connections can be made by the wearer after the garment is positioned on the body.

It has been found that optimum muscle contractions are produced when the electrode pairs are placed at specific locations over the muscle group. Because all humans have the same muscle structures, which varies only due to the size of the individual and their muscle build, it was determined that a garment having electrodes of predetermined size could be used on all individuals of a similar stature. With the electrode assembly 10 heretofore described, the stimulation level (current density) and area of stimulation can be more accurately controlled. As a result, a standard garment could be provided having such electrodes, which garment would be suitable for all individuals of similar stature and would provide accurate, repeatable stimulation. Also important, a garment of a stretchable fabric would accommodate muscle development and growth.

With respect to the dimensions of the electrode 14 used on the garments, the electrodes 14 placed on limb portions of the garments (arms and legs) preferably have a length equal to 20% to 30% of the girth of the limbs. Because the electric field produced by the electrode penetrates through skin, fat, and connective tissue unevenly due to the differences in electrical impedances of these tissues, it has been found through experience that stimulating 20% to 30% of the circumference of the extremity recruits (excites) a majority of muscle fibers without recruiting unwanted fibers. In most situations, a 2"×4" electrode meets such requirements. With respect to electrodes positioned on the torso, such electrodes provide satisfactory stimulation.

With respect to electrode assemblies 10 used on garments, such assemblies 10 may be individually connected to a source of electrical stimulation (not shown) or may be connected to each other by insulated connector leads 88. The body garments shown in FIGS. 6 and 7 enable electrode assemblies 10 to be accurately located at specific body locations in a simple, repeatable expedient manner.

The present invention has been described with respect to preferred embodiments. Modifications and alterations that would occur to others based upon their reading and understanding of the specification. For example, electrode assembly 10 has been described with respect to a rectangular shaped electrode 14. It will be appreciated that electrode 14 may be circular, oval or have some other shape, and that overlying layer 16 may be dimensioned accordingly. Still further, electrode assembly 10 has been described with respect to an adhesive material securing layer 16 to layer 12. As an alternative, extending portion 44 may be sewn onto layer 12 to secure electrode 14 therebetween. In this respect, a sealant may be provided around the periphery of element 14 to prevent migration of the conductive fluid 54 into the interstices of the fabric layer 12. It is intended that all such modifications and alterations be included insofar as they come within the scope of the patent as claimed or the equivalence thereof.

Having thus described invention, the following is claimed:

1. A garment for transcutaneous neural stimulation comprising:
   a non-conductive, knit fabric material defining a first layer;
   at least one flexible, generally flat electrically conductive electrode having an upper surface and a generally planar lower surface in confronting relationship with said fabric material, said electrode connectable to a source of electrical stimulation;
   a second layer of a non-conductive material overlying the upper surface of said electrode, said second layer dimensioned such that a portion thereof extends a predetermined distance beyond the periphery of said electrode;
   a layer of adhesive material disposed between said second layer and said first layer for securing said second layer to said first layer, said electrode being confined between said first layer and said second layer wherein a generally flat pocket to receive a conductive fluid is defined between said first layer and said lower surface of said electrode;
   said adhesive layer securing said first layer to said second layer defining a boundary around the entire periphery of said electrode for preventing migration of said conductive fluid beyond the periphery of said electrode.

2. A garment as defined in claim 1 wherein said first and second layers are sewn together along the periphery of said electrode.

3. A garment as defined in claim 1 wherein said boundary is comprised of said adhesive penetrating said first layer of knit fabric and hardening therein.

4. A garment as defined in claim 1 wherein the lower surface of electrode includes at least one groove therealong.

5. A garment as defined in claim 1 wherein said electrode is formed of a rubber-like, carbon material and includes an enlarged portion having a receptacle therein adapted to receive a plug.

6. A garment as defined in claim 1 wherein said electrode is rectangular in shape.

7. A garment as defined in claim 1 wherein said electrode is circular in shape.

8. A garment as defined in claim 1 wherein said first layer is formed of a blend of 90% nylon and 10% polyester.

9. A garment for transcutaneous neural stimulation comprised of:
   an electrically non-conducting knit fabric material having an inner side to be positioned against a patient's body and an outer side;
   at least one flexible, generally flat electrically conductive electrode having an upper surface and a generally planar lower surface in confronting relationship with a portion of said outer side of said fabric material;
   a layer of a non-conductive material overlying the upper surface of said electrode, said layer dimensioned such that a portion thereof extends a predetermined distance beyond the periphery of said electrode;
   a layer of adhesive material disposed between said second layer and said first layer for securing said layer to said garment, said electrode being confined between said first layer and said second layer wherein a generally flat pocket to receive a conductive fluid is defined between said fabric material and said lower surface of said electrode
   said adhesive layer securing said first layer to said second layer defining a boundary around the entire periphery of said electrode for preventing migration of said conductive fluid beyond the periphery of said electrode.

10. A garment as defined in claim 9 wherein said electrode is generally rectangular in shape.

11. A garment as defined in claim 10 wherein said garment includes limb portions for covering the arms and legs of the wearer, said limb portions including at least one electrode assembly thereon, said electrode assembly disposed at a predetermined position on the surface of the wearer's skin and dimensioned to overlay a predetermined amount of the girth of said limb portions.

12. A garment as defined in claim 11 wherein said electrode assembly overlays 20% to 30% of the girth of said limb portions.

13. A method of delivering electrical stimuli to the skin of a living body comprising the steps of:

positioning an electrode assembly on the body, said electrode assembly having a first layer of a non-conductive, knit fabric material, a flexible, generally flat electrically conductive electrode having an upper surface and a generally planar lower surface in confronting relationship with a portion of said fabric material, said electrode connectable to a source of electrical stimulation, a second layer of a non-conductive material overlying the upper surface of said electrode, said second layer dimensioned such that a portion thereof extends a predetermined distance beyond the periphery of said electrode, a layer of adhesive material disposed between said second layer and said first layer for securing said second layer to said first layer, said electrode being confined between said first layer and said second layer wherein a generally flat pocket to receive a conductive fluid is defined between said first layer and said lower surface of said electrode, said adhesive layer securing said first layer to said second layer defining a boundary around the periphery of said electrode for preventing migration of said conductive fluid beyond the periphery of said electrode;

introducing an electrically conductive fluid into said flat pocket;

connecting said electrode to a source of electrical stimulation means; and electrically operating said electrical stimulation means.

14. A method of delivering electrical stimuli to the skin of a living body comprising the steps of:

applying an electrically conductive fluid to a garment made of an electrically non-conductive, stretchable fabric material having an inner side to be positioned against the skin of the body and outer side, said garment including at least one generally flat, electrically conductive electrode having a generally planar lower surface in confronting relationship with a portion of said outer side of said fabric material, means for securing said electrode to said fabric material wherein a generally flat cavity is defined between said fabric material and said electrode, and means defining a boundary around the periphery of said electrode for preventing migration of said fluid beyond the periphery of said electrode, said conductive fluid penetrating through the fabric material confronting said electrode when introduced into said cavity;

putting said garment on said body;

connecting said electrode to a source of electrical stimulation means;

electrically operating said electrical stimulation means.

15. A method as defined in claim 14 wherein said garment includes a plurality of electrodes.

16. A method as defined in claim 14 wherein said conductive fluid is inserted into said cavity through said fabric material.

17. A garment for transcutaneous neural stimulation comprising:

a garment including limb portions for covering the limbs of the wearer, said garment made on an electrically non-conductive, stretchable, knit fabric material having an inner side to be positioned against a patient's body and an outer side;

at least one flexible, generally flat electrically conductive electrode disposed on each of said limb portions, said electrode having a generally planar lower surface in confronting relationship with a portion of said outer side of said fabric material wherein said planar lower surface is in electrically conductive contact with the patient's body when an electrically conductive fluid is introduced below said lower surface, said electrode covering at lest 20% of the girth of limb associated therein; and means for confining said conductive fluid to a predetermined area below said electrode.

* * * * *